United States Patent [19]

Stevens et al.

[11] 3,972,897
[45] Aug. 3, 1976

[54] MOSQUITO LARVICIDE
[75] Inventors: Kenneth L. Stevens, Walnut Creek; Leonard Jurd, Berkeley, both of Calif.
[73] Assignee: The United States of America as represented by the Secretary of Agriculture, Washington, D.C.
[22] Filed: Oct. 30, 1975
[21] Appl. No.: 627,328

Related U.S. Application Data
[62] Division of Ser. No. 554,053, Feb. 27, 1975, Pat. No. 3,954,991.

[52] U.S. Cl. ............................................. 260/340.5
[51] Int. Cl.² ..................................... C07D 317/48
[58] Field of Search ................................ 260/340.5

Primary Examiner—Ethel G. Love
Attorney, Agent, or Firm—M. Howard Silverstein; Max D. Hensley; William Takacs

[57] ABSTRACT

Limonene (or alpha-pinene) is condensed with sesamol under aqueous acidic conditions to produce a mixture of two novel compounds which are useful as mosquito larvicides.

4 Claims, No Drawings

MOSQUITO LARVICIDE

This is a division of our copending application Ser. No. 554,053, filed Feb. 27, 1975, now U.S. Pat. No. 3,954,991.

DESCRIPTION OF THE INVENTION

The invention relates to and has among its objects the provision of new organic compounds and their use as mosquito larvicides. Further objects of the invention will be evident from the following description wherein parts and percentages are by weight unless otherwise specified. The abbreviation ppm used herein refers to parts per million.

One of the ways of controlling insect populations is to kill the insect larvae. Generally, a larvicide is applied to the breeding places or habitat of the insects where it destroys substantial numbers of the larvae.

We have discovered that certain new organic compounds are effective as mosquito larvicides. When the compounds of the invention are applied to the habitat of the mosquito, the larval population is substantially reduced.

The compounds of the invention contain the following nucleus:

I.

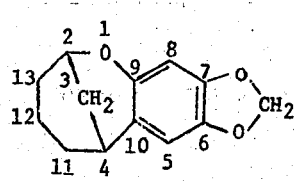

One aspect of the invention concerns the provision of a novel composition of matter being a mixture of two position isomers (ML-1 and ML-2). These isomeric compounds are represented by the following formulas:

II.
(ML-1)

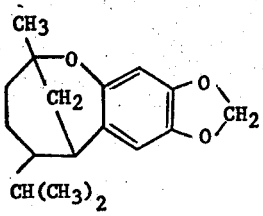

III.
(ML-2)

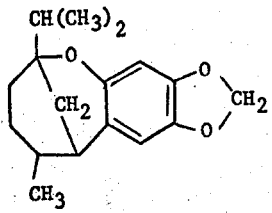

As can be seen from the formulas, ML-1 and ML-2 differ in the positions of an isopropyl group and a methyl group. In ML-1, the methyl group is in position 2 and the isopropyl group is in position 11. In ML-2, the methyl group is in position 11 and the isopropyl group is in position 2.

Referring to Formulas II and III, each of the methyl and isopropyl substituents may also be in either $\alpha$ or $\beta$ configuration. The compositions of the invention may contain all of the stereoisomers of ML-1 and ML-2, or they may contain only one stereoisomer of each of the said position isomers.

The mixture of ML-1 and ML-2 is highly effective in killing mosquito larvae. Generally, for such purpose the mixture is applied to the breeding places of the mosquitos in a concentration about 1 to 10 ppm. Because the mixture of ML-1 and ML-2 is effective in very minor concentrations, it is preferred that it be dissolved or suspended in an appropriate carrier prior to application to the breeding centers. The solution or suspension increases the bulk of the mixture and thus allows small amounts of ML-1 and ML-2 to be administered to the mosquito's habitat. Solvents appropriate for this aspect of the invention should be highly volatile, such as acetone, ethyl ether, ethanol, benzene, xylene, and the like.

Usually, the composition of the invention contains ML-1 and M-2 in approximately equal proportions. However, it is within the compass of the invention to use a mixture wherein either ML-1 or ML-2 predominates. In addition, it is also within the scope of the invention to use either ML-or ML-2 individually as a mosquito larvicide.

Another aspect of the invention concerns the method of synthesizing ML-1 and ML-2. This involves condensing limonene (or alphapinene) with sesamol under aqueous acidic conditions. The condensation is generally carried out under reflux, which is maintained for approximately 24 hours. Usually, an organic acid, preferably formic acid, is employed and the concentration of acid in water is about 50%. Other acids which may be used in accordance with the invention are acetic acid, propionic acid, citric acid, tartaric acid, and the like. The condensation produces the desired mixture of ML-1 and ML-2, which are obtained free of unreacted limonene and sesamol by conventional purification steps such as extraction and distillation under reduced pressure.

The synthesis of the invention is illustrated by the following formulas:

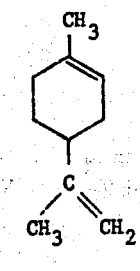

Limonene

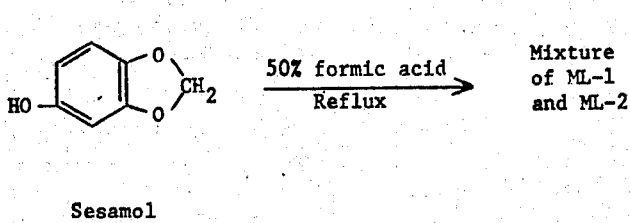

Sesamol

The mixture of ML-1 and ML-2 is useful in such form, as explained above, as a mosquito larvicide. It is within the compass of the invention, moreover, to fractionate the mixture into its ML-1 and ML-2 components or even to apply a higher degree of fractionation to isolate individual stereoisomers of either ML-1 or ML-2. For the fractionations one may use such known techniques as fractional distillation, preparative glc, or column chromatography.

EXAMPLES

The invention is further demonstrated by the following illustrative examples.

EXAMPLE 1

Condensation of Limonene with Sesamol

A mixture of sesamol (13.8 g., 0.1 mole), limonene (13.6 g., 0.1 mole) and 500 ml. of 50% formic acid was refluxed for 24 hours and then cooled to room temperature. The mixture was extracted with ether and yielded an oil, which distilled at 140°–145°C. at 150 $\mu$ Hg. The distillate (23.8 g., 87%) was a mixture of Ml-1 and ML-2, which were separated by column chromatography on activity III alumina. The column was eluted with a 95:5 mixture of Skelly F:ether. (Skelly F is a mixture of petroleum hydrocarbons boiling between 30° and 60°C.) ML-2 was eluted first as an oil and had the following nuclear magnetic resonance (nmr) spectrum at 100 MHz in deuterated chloroform: a doublet (6 protons) at $\delta$ 0.95 (J = coupling constant = 7.0 Hz), a doublet (3 protons) at $\delta$ 1.09 (J = 7.0 Hz), a multiplet (1 proton) at $\delta$ 2.57 (8 Hz half width), a singlet (2 protons) at $\delta$ 5.80, a singlet (1 proton) at $\delta$ 6.35, and a singlet (1 proton) at $\delta$ 6.42. High resolution mass spectrometry—found molecular weight of 274.1567—$C_{11}H_{22}O_3$ requires 274.1569.

ML-1 was eluted after ML-2 and exhibited the following nmr spectrum at 100 Hz in deuterated chloroform: a doublet (3 protons) at $\delta$ 0.94 (J = 6 Hz), a doublet (3 protons) at $\delta$ 1.03 (J = 6.0 Hz), a singlet (3 protons) at $\delta$ 1.29, a multiplet (1 proton) at $\delta$ 2.90 (8 Hz half width), a singlet (2 protons) at $\delta$ 5.78, a singlet (1 proton) at $\delta$ 6.34, and a singlet (1 proton) at $\delta$ 6.39.

EXAMPLE 2

Mosquito Larvicide Test

A mixture of ML-1 and ML-2 (approximately 50:50) prepared as described in Example 1 was dissolved in acetone. The solution was added to water such that the final concentration of the mixture (ML-1 and ML-2) on the water was 10 ppm. Early fourth-instar larvae of *Anopheles quadrimaculatus* Say were exposed to the treated water and mortality was determined after 24 hours of exposure.

The above experiment was repeated with the following change: The ML-1-ML-2 mixture was added to the water to produce a final concentration of 1 ppm. The results are summarized in the table below.

Table 1

| Mosquito larvicide | Concentration (ppm) | Mortality after 24 hrs. (%) |
|---|---|---|
| 50:50 ML-1:ML-2 | 10 | 92 |
| 50:50 ML-1:ML-2 | 1 | 36 |

Having thus described our invention, we claim:

1. A compound of the structure

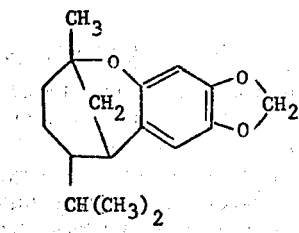

2. A compound of the structure

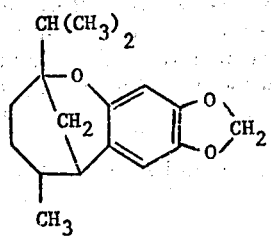

3. A mixture of the compounds of the structures

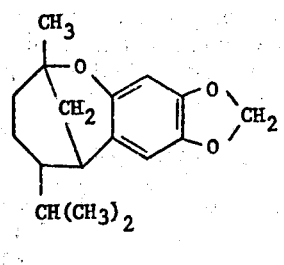

and

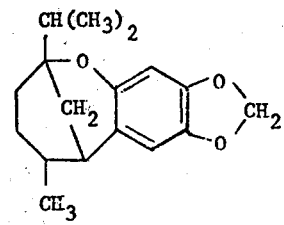

4. The mixture of claim 3 wherein the designated compounds are in approximately equal proportions by weight.

* * * * *